United States Patent [19]

Kasai et al.

[11] Patent Number: 4,991,601
[45] Date of Patent: Feb. 12, 1991

[54] HOLDER FOR BLOOD SAMPLE TUBE

[75] Inventors: Masaaki Kasai; Sakae Yamazaki; Kazuhisa Sensyu, all of Yamanashi, Japan

[73] Assignee: Terumo Kabushiki Kaisha, Tokyo, Japan

[21] Appl. No.: 350,541

[22] Filed: May 11, 1989

[30] Foreign Application Priority Data

May 20, 1988 [JP] Japan .............................. 63-121835

[51] Int. Cl.$^5$ .......................... B65D 81/00; A61B 5/00
[52] U.S. Cl. .................................... 128/763; 128/766; 128/764; 604/198
[58] Field of Search .............................. 128/760-766; 206/363-367; 604/198

[56] References Cited

U.S. PATENT DOCUMENTS

| | | | |
|---|---|---|---|
| 4,295,476 | 10/1981 | Quaas | 128/764 |
| 4,326,541 | 4/1982 | Eckels | 128/764 X |
| 4,412,548 | 11/1983 | Hoch | 128/764 |
| 4,592,744 | 6/1986 | Jagger et al. | 128/763 X |
| 4,781,700 | 11/1988 | Vicario | 128/760 X |
| 4,871,355 | 10/1989 | Kikkawa | 128/763 X |

Primary Examiner—Robert A. Hafer
Assistant Examiner—Kerry Owens
Attorney, Agent, or Firm—Frishauf, Holtz, Goodman & Woodward

[57] ABSTRACT

A blood sample tube holder for holding a blood sample tube includes a holder body having a needle joint on one end for connection to a blood sample collecting needle, the holder body having an open opposite end. The holder body has a plurality of elastic and flexible lands on an inner wall surface thereof. The lands have radially innermost surfaces arranged such that when the blood sample tube is inserted into the holder body through the open opposite end, the lands are engaged and elastically deformed by the blood sample tube for an increased area of contact with the blood sample tube for holding the blood sample tube in the holder body.

11 Claims, 4 Drawing Sheets

HOLDER FOR BLOOD SAMPLE TUBE

BACKGROUND OF THE INVENTION

The present invention relates to a holder for holding a blood sample tube, and more particularly to a blood sample tube holder for preventing a kickback in a blood sample tube having a small resistance to being pierced by a needle, i.e., a small piercing resistance.

Blood sampling systems are used in clinical examination in hospitals or other medical facilities. In such blood sampling systems, a blood sample tube holder is combined successively with various blood sample tubes such as those for use examining blood serum, blood cells, blood sugar, and coagulants, and blood samples are obtained from a patient through a multiple needle mounted on the blood sample tube holder and collected in the blood sample tubes, respectively.

A blood sample tube, such as a decompressive blood sample tube, comprises a bottomed tube of glass or plastics and a rubber plug in the bottomed tube.

In use, a decompressive blood sample tube of such a construction is inserted into a cylindrical blood sample tube holder, and a rubber piercing portion of a multiple needle penetrates the rubber plug of the blood sample tube. The rubber plug which the rubber piercing portion of the multiple needle pierces is relatively thick as it is required to have a gas barrier and a resealing capability. Since the rubber plug presents a strong resistance to being pierced by the rubber piercing portion, the tendency of the decompressive blood sample tube to return to its original position immediately after the rubber plug is pierced by the needle, i.e. a phenomenon called a "kickback", is small.

If an automatic blood serum separator is used, it is preferable to employ a decompressive blood sample tube which can be used without detaching its rubber plug.

FIG. 1 of the accompanying drawings shows a decompressive blood sample tube 10 proposed by the applicant. The decompressive blood sample tube 10 comprises a bottomed tube 2 and a sealing assembly 8 placed over the open end of the bottomed tube 2 and composed of a film member 4 and a resealing rubber member 6. In use, the needle of an automatic blood serum separator directly pierces the sealing assembly 8. The proposed decompressive blood sample tube 10 does not employ any rubber plug, but is prevented from getting contaminated from an external source. The decompressive blood sample tube 10 is inserted in a cylindrical blood sample tube holder 14 with a multiple needle 12 mounted thereon The multiple needle 12 comprises a blood vessel piercing portion 16, a rubber piercing portion 20 projecting into the holder 14 and covered with a rubber sheath 18, and a needle base 22 supporting the blood vessel piercing portion 16 and the rubber piercing portion 20 on its opposite ends. When the multiple needle 14 is inserted into the blood sample tube holder 14, the rubber piercing portion 20 penetrates the rubber sheath 18 and the sealing assembly 8. Blood drawn from the patient through the blood vessel piercing portion 16 flows through the multiple needle 12 into the decompressive blood sample tube 10.

The film member 4 provides a gas barrier capability whereas the resealing rubber member 6 provides a resealing capability. Because the resistance presented by the sealing assembly 8, which is used in place of a conventional rubber plug, to being pierced by the rubber piercing portion 20 of the multiple needle 12 is generally weak, the decompressive blood sample tube 10 is subject to a kickback under the resiliency of the rubber sheath 18 on the rubber piercing portion 20, and the sealing assembly 8 may not be sufficiently pierced by the rubber piercing portion 20 of the multiple needle 12.

To prevent such a kickback, it is necessary to keep the outer wall surface of the sealing assembly 8 or the bottomed tube 2, or a flange 24 of the bottomed tube 2, firmly fitted in the blood sample tube holder 14. One arrangement for meeting this requirement is to provide ribs on the inner wall surface of the holder 14 for secure fitting engagement with the bottomed tube 2. According to this structure, the force required to fit the decompressive blood sample tube 10 into the blood sample tube holder 14 tends to be excessively increased, and a certain increased level of finishing accuracy is required of the holder 14 and the tube 10 to maintain the force required to fit the tube 10 into the holder 14 at a certain constant level. More specifically, for collecting a blood sample from a patient, the blood vessel piercing portion of the multiple needle 12 mounted on the holder 14 is inserted into a blood vessel of the patient, and then the decompressive blood sample tube 10 is inserted into the blood sample tube holder 14 until the rubber piercing portion 16 of the multiple needle 12 penetrates the sealing assembly 8. While the tube 10 is being inserted into the holder 14, the force required to fit the tube into the holder 14 may be abruptly increased, or a large force may be needed to pull the tube 10 out of the holder 14 after a blood sample is obtained in the tube 10. The increased level of finishing accuracy required of the holder 14 and the tube 10 results in an increase in the cost of manufacture of blood sample tube holders and blood sample tubes.

SUMMARY OF THE INVENTION

It is a primary object of the present invention to provide a blood sample tube holder which allows a blood sample tube which has a relatively weak resistance to being pierced by a needle to be fitted into the blood sample tube holder under a progressively increasing force for thereby keeping the blood sample tube fitted reliably and firmly in the blood sample tube holder against a kickback, and which can be manufactured with ease.

Another object of the present invention is to provide a blood sample tube holder for holding a blood sample tube, comprising a holder body having a needle joint on one end for connection to a blood sample collecting needle, said holder body having an open opposite end, said holder body having an elastic and flexible land on an inner wall surface thereof, said land having a radially innermost surface arranged such that when the blood sample tube is inserted into said holder body through said open opposite end, said land is engaged and elastically deformed by the blood sample tube for an increased area of contact with the blood sample tube for holding the blood sample tube in said holder body.

Still another object of the present invention is to provide a blood sample tube holder wherein said land has a length of at least 5 mm in the direction in which the blood sample tube is inserted in said holder body.

Yet another object of the present invention is to provide a blood sample tube holder wherein said land has a width in a circumferential direction of said holder body, said width being as large as at least 1/10 of the circumferential length of said inner wall surface.

A further object of the present invention is to provide a blood sample tube holder wherein said land has a length of at least 5 mm in the direction in which the blood sample tube is inserted in said holder body, and wherein said land has a width in a circumferential direction of said holder body, said width being as large as at least 1/10 of the circumferential length of said inner wall surface.

A still further object of the present invention is to provide a blood sample tube holder wherein said land and said holder body are integrally formed with each other, said land having a thickness smaller than the thickness of said holder body.

A yet further object of the present invention is to provide a blood sample tube holder according to claim 1, wherein said holder body has a plurality of said lands, the diameter of an imaginary circle which passes through the radially innermost surfaces of the lands being smaller than the diameter of a portion of the blood sample tube which engages said lands.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
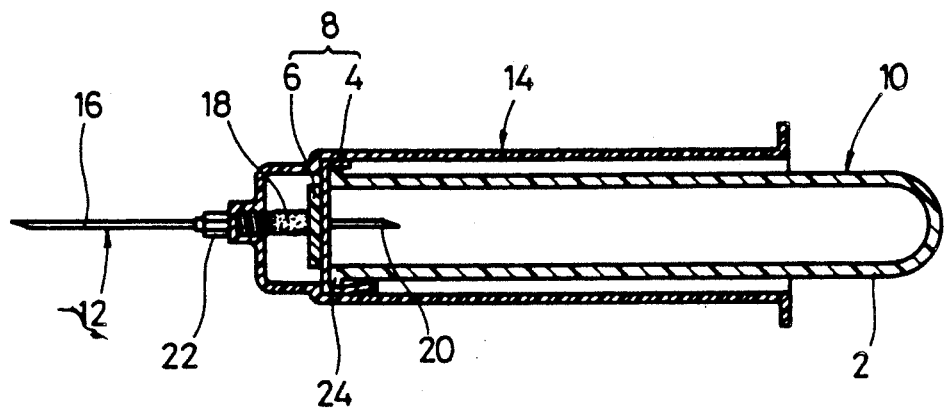
FIG. 1 is a longitudinal cross-sectional view of a conventional blood sample tube holder which is used with a blood sample tube.
Figure 2:
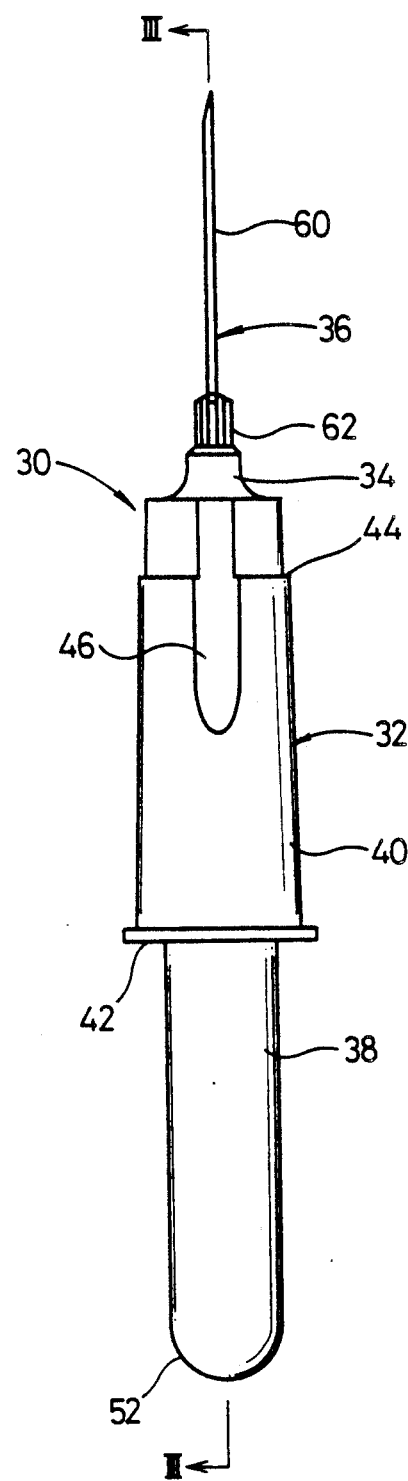
FIG. 2 is a front elevational view of a blood sample tube holder according to the present invention, used with a blood sample tube.

FIG. 2 shows a blood sample collecting instrument 30 comprising a blood sample tube holder 32, a multiple needle 36 mounted on a needle joint 34 on one end of the blood sample tube holder 32, and a decompressive blood sample tube 38 inserted in the blood sample tube 32 through an opening in the other end of the holder 32.

The blood sample tube holder 32 is made up of plastics such as polypropylene or the like. The blood sample tube holder 32 includes a substantially cylindrical holder body 40 with the needle joint 34 integrally formed with one end thereof, the needle joint 34 having internal screw threads 41 on its inner peripheral surface (see FIG. 3). The other end of the blood sample tube holder 32 is open and has a flange 42 for facilitating blood sample collecting operation.

Figure 4:
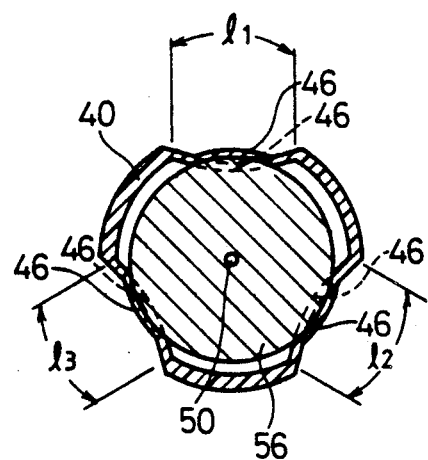
FIG. 4 is an enlarged transverse cross-sectional view taken along line IV—IV of FIG. 3.

The holder body 40 is progressively tapered slightly from the flange 42 toward the needle joint 34 and has a step 44 positioned near the needle joint 34 and adjoining a smaller-diameter portion of the holder body 40. As also shown in FIG. 4, the holder body 40 has three angularly equally spaced, radially inwardly projecting lands 46 on the inner wall surface thereof, the lands 46 extending axially from a substantially longitudinally central portion of the holder body 40 toward the needle joint 34. The lands 46 have respective widths $l_1$, $l_2$, $l_3$ in the circumferential direction of the holder body 40, the sum of these widths $(l_1+l_2+l_3)$ being preferably 1/10 or more of the circumferential length of the inner wall surface of the holder body 40. Each of the lands 46 should preferably be of a length $l_4$ of at least 5 mm in the direction in which the decompressive blood sample tube 38 is inserted into the holder 32. If the axial length of the lands 46 were smaller than 5 mm, since it is necessary to progressively increase the force required to fit the tube 38 into the holder 32 for smoothly fitting the tube 38 into the holder 32, the lands 46 would be too short to increase such force from zero to a prescribed level, and hence a prescribed force level would not be attained.

The lands 46 may be integrally formed with the blood sample tube holder 14 when it is molded. Therefore, the lands 46 may easily be made thinner than the other portions of the holder body 40. The lands 46 are shaped arcuately to have their radially innermost surfaces positioned as indicated by the dotted lines in FIG. 4 so that when the decompressive blood sample tube 38 is inserted in the holder body 40, the radially innermost surfaces of the lands 46 are engaged by the outer peripheral surface of a radially outwardly extending flange around an open end of the inserted tube 38 and elastically deformed slightly radially outwardly as indicated by the solid lines in FIG. 4 to apply reactive forces to the decompressive blood sample tube 38. More specifically, the lands 46 are formed so as to be elastic and flexible. When the decompressive blood sample tube 38 is inserted into the holder body 40, the lands 46 are elastically flexed by pressed engagement with the tube 38 to keep the tube 38 in place through an increased area of contact between the holder body 40 and the tube 38. It is preferable for each of the lands 46 to flex a distance of 0.1 mm or greater in the radial direction. Stated otherwise, the lands 46 should be shaped such that the diameter of an imaginary circle passing through the radially innermost surfaces of the lands 46 is 0.2 mm smaller than the diameter of the flange of the decompressive blood sample tube 38. When the decompressive blood sample tube 38 is inserted into the blood sample tube holder 32, the lands 46 are elastically deformed to exert a progressively increasing resilient force to the tube 38 to fit the tube 38 in the holder body 40. When the decompressive blood sample tube 38 is inserted a predetermined length into the blood sample tube holder 32, the tube 38 is fittingly retained reliably in the holder 32.

With the decompressive blood sample tube 38 inserted in the holder body 40, the tube 38 is held in fitting engagement with the lands 46 under an increased force to reduce the resistance (piercing resistance) experienced when a sealing assembly 48 (described later on) is pierced by a rubber piercing member 50 of a multiple needle 36. The measured resistance against the force tending to push the decompressive blood sample tube 38 into the holder body 40 ranged from 600 to 1000 gf, whereas the measured resistance against the force tending to pull the decompressive blood sample tube 38 out of the holder body 40 ranged from 300 to 500 gf (the decompressive blood sample tube 38 was pushed in or pulled out at a speed of 500 mm/min. without the multiple needle 36 being attached).

The decompressive blood sample tube 38 comprises a bottomed tube 52 having one end opened and the other end closed, an anticoagulant 54 placed in the bottomed tube 52, and the sealing assembly 48 which is disposed over the open end of the bottomed tube 52 to sea the interior space thereof. The sealing assembly 48 comprises a film 56 extending over the open end of the bottomed tube 52 and disposed around the flange thereof. Therefore, the diameter of the flange of the tube 38, as referred to above should be interpreted to mean the maximum outside diameter of the flange covered with the film 56.

The bottomed tube 52 closed by the sealing assembly 48 may not necessarily be decompressed, but should preferably be decompressed to a certain degree depending on the amount of blood to be sampled.

As shown in FIG. 2, the bottomed tube 52 is in the shape of a test tube and made of glass or a plastic material having a gas barrier capability, such as acrylonitrile, polyethylene terephthalate, or the like.

The anticoagulant 54 is used to prevent the blood sample from being coagulated after the blood sample is collected in the blood sample tube 38 or while the blood is being examined The anticoagulant 54 may for example be EDTA-2K or the like.

The film 56 has a gas barrier capability and is made of aluminum foil, or a film of any of various materials which is coated with an aluminum layer by evaporation, or a film of any of various materials which is coated with a gas barrier material such as polyvinylidene chloride, polyvinyl alcohol, an ethylene-vinyl alcohol copolymer, or the like. An adhesive layer may be applied to the decompressive blood sample tube 38, and the sealing assembly 48 may be bonded to the tube 38 by the adhesive layer.

The sealing assembly 58 also includes a resealing rubber member 58 bonded to the film 56. The resealing rubber member 58 is made of a material such as synthetic rubber, natural rubber, or thermoplastic elastomer which can seal the interior space of the decompressive blood sample tube 38 again after the multiple needle 36 is pulled out of the sealing assembly 48.

Figure 3:
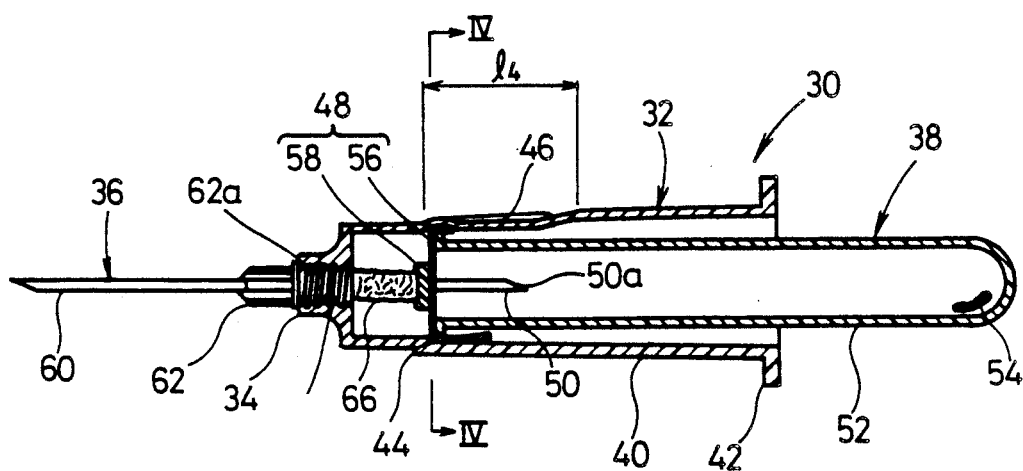
FIG. 3 is a longitudinal cross-sectional view taken along line III—III of FIG. 2.

In use, the decompressive blood sample tube 38 is inserted in the blood sample tube holder 32 on which the multiple needle 36 is mounted, as shown in FIG. 3. The multiple needle 36 comprises a blood vessel piercing member 60 for piercing a blood vessel, a rubber piercing member 50 for piercing the resealing rubber member 58 and the film 56, and a base portion 62 supporting the blood vessel piercing portion 60 and the rubber piercing portion 50 on its opposite ends. The base portion 62 has external screw threads 62a on its outer peripheral surface adjacent to the rubber piercing portion 50 for threaded engagement in the blood sample tube holder 32. As shown in FIG. 3, the multiple needle 36 is threaded in the needle joint 34 of the blood sample tube holder 32. A thin rubber tube or tip 66 is mounted on the rubber piercing portion 50 in surrounding relation thereto substantially up to its pointed distal end 50a when the rubber sheath 66 is in its free state.

The blood sample tube holder 32 will be used as follows:

As shown in FIG. 3, the multiple needle 36 is threaded in the blood sample tubeholder 32 and then the blood vessel piercing portion 60 of the multiple needle 36 is inserted into a blood vessel of a patient. The decompressive blood sample tube 38 is thereafter inserted into the holder body 40 of the blood sample tube holder 32. When the decompressive blood sample tube 38 is inserted to a substantially central area in the holder body 40, the sealing assembly 48 of the tube 38 engages the lands 46 on the inner wall surface of the holder body 40. Upon continued insertion of the tube 38, the decompressive blood sample tube 38 is subjected to a progressive resilient force exerted from the lands 46 since the tube 38 is forcibly inserted against the resiliency of the lands 46, while the rubber piercing portion 50 successively pierces the rubber sheath 66, the resealing rubber member 58, and the film 56. At this time, the rubber sheath 66 and the sealing assembly 48 apply repulsive forces to the decompressive blood sample tube 38, but the tube 38 is not pushed back due to a kickback because the tube 38 is firmly fitted in the holder body 40 by the lands 46 and undergoes the piercing resistance from the resealing rubber member 58 and the film 56

Figure 5:
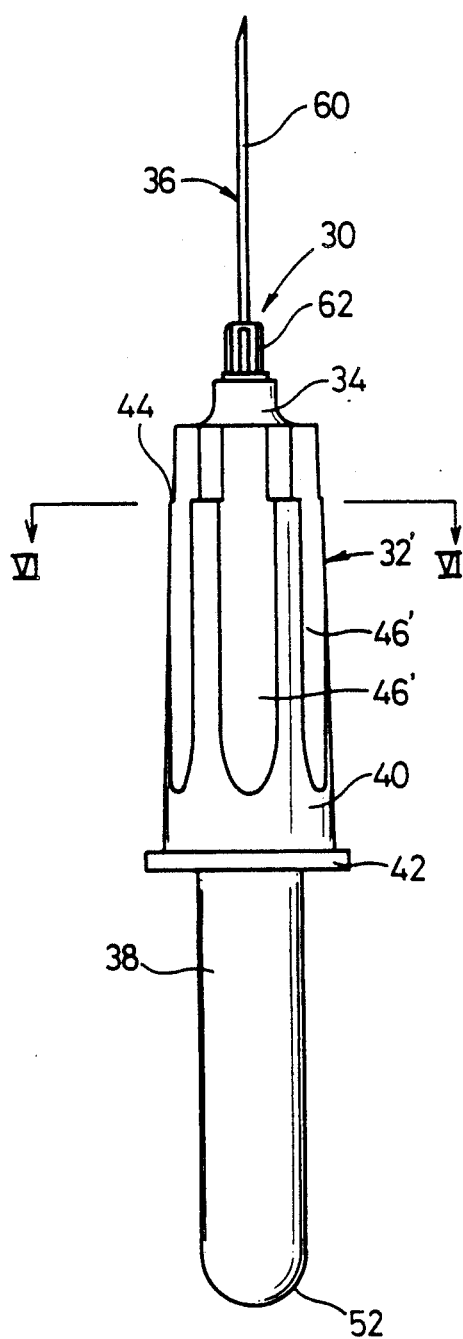
FIG. 5 is a front elevational view of a blood sample tube holder according to another embodiment of the present invention, used with a blood sample tube.
Figure 6:
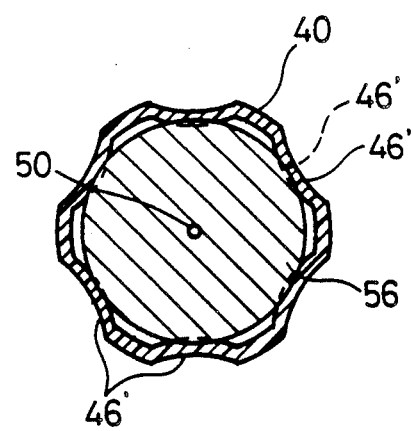
FIG. 6 is an enlarged transverse cross-sectional view taken along line VI—VI of FIG. 5.

Blood is then collected from the blood vessel in a quantity corresponding to the decompression in the decompressive blood sample tube 38. The collected blood in the decompressive blood sample tube 38 is thereafter sampled by an automatic blood serum separator or the like (not shown) for blood examination of various types FIGS. 5 and 6 show a blood sample tube holder according to another embodiment of the present invention. The blood sample tube holder of this embodiment differs from the blood sample tube holder according to the previous embodiment in that the blood sample tube holder, denoted at 32', has six lands 46' projecting radially inwardly. The other details shown in FIGS. 5 and 6 are the same as those of the previous embodiment and will not be described.

With the present invention, as described above, a blood sample tube holder includes a holder body having a needle joint on one end for connection to a blood sample collecting needle, the holder body being open at the other end. The holder body has elastic and flexible lands on its inner wall surface, the lands having radially innermost surfaces arranged such that when a blood sample tube is inserted into the holder body through the open end, the lands are engaged and elastically deformed by the blood sample tube for an increased area of contact with the blood sample tube for holding the blood sample tube in the holder body. The lands as they are elastically deformed then apply repulsive forces to the blood sample tube. When the blood sample tube is inserted into the blood sample tube holder, therefore, since the force tending to fit the blood sample tube in the blood sample tube holder is progressively increased under resilient forces from the lands, the blood sample tube is prevented from being pushed back by a kickback. Because the blood sample tube is firmly fitted in the blood sample tube holder, a kickback is prevented from occurring even if the blood sample tube exerts a weak piercing resistance to the blood sample collection needle. The elastic lands for tightly holding the blood sample tube in the blood sample tube holder do not require a high degree of finishing accuracy for the blood sample tube holder and the blood sample tube. Therefore, the blood sample tube holder according to the present invention can be manufactured easily and inexpensively.

With the length of the lands being at least 5 mm in the direction in which the blood sample tube is inserted in the blood sample tube holder, the blood sample tube can be smoothly and softly inserted while being firmly fitted in the blood sample tube holder.

Although certain preferred embodiments have been shown and described, it should be understood that many changes and modifications may be made therein without departing from the scope of the appended claims.

What is claimed is:

1. A blood sample tube holder for holding a blood sample tube, comprising:

a holder body having a needle joint on one end for connection to a blood sample collecting needle, said holder body having an open end opposite said one end, and at least one elastic and flexible land on an inner wall surface thereof, said at least one land having a radially innermost surface arranged such that when a blood sample tube is inserted into said holder body through said open end, said at least one land is engaged and elastically deformed by said blood sample tube so as to increase contact area between said at least one land and said blood sample tube, thereby firmly holding said blood sample tube in said holder body and preventing said blood sample tube from being pushed or kicked back out of said holder body.

2. A blood sample tube holder according to claim 1, wherein said at least one land has a length of at least 5 mm in the direction in which the blood sample tube is inserted in said holder body.

3. A blood sample tube holder according to claim 1, wherein said at least one land has a width in a circumferential direction of said holder body, being as large as at least 1/10 of the circumferential length of said inner wall surface.

4. A blood sample tube holder according to claim 1, wherein said at least one land has a length of at least 5 mm in the direction in which the blood sample tube is inserted in said holder body and wherein said at least one land has a width in a circumferential direction of said holder body being as large as at least 1/10 of the circumferential length of said inner wall surface.

5. A blood sample tube holder according to claim 1 wherein said at least one land and said holder body are integrally formed with each other, said at least one land having a thickness smaller than the thickness of said holder body.

6. A blood sample tube holder according to claim 1, wherein said at least one land comprises a plurality of lands, the diameter of an imaginary circle which passes through the radially innermost surfaces of the lands being smaller than the diameter of a portion of the blood sample tube which engages said lands.

7. A blood sample tube holder according to claim 1, wherein said at least one land is arcuate.

8. A blood sample tube holder according to claim 7, wherein said at least one arcuate land radially projects inward toward an interior portion of said holder body.

9. A blood sample tube holder according to claim 1, wherein said at least one land extends from the vicinity of said one end having a needle point.

10. A blood sample holder according to claim 9, wherein said at least one land has a length of at least 5mm in the direction in which the blood sample tube is inserted in said holder body.

11. A blood sample holder according to claim 1, wherein said at least one land comprises a plurality of lands spaced circumferentially around said inner wall surface of said holder body.

* * * * *

UNITED STATES PATENT AND TRADEMARK OFFICE
CERTIFICATE OF CORRECTION

PATENT NO. : 4,991,601
DATED : February 12, 1991
INVENTOR(S) : KASAI et al It is certified that error appears in the above-identified patent and that said Letters Patent is hereby corrected as shown below:

Column 1, line 52, after "thereon" insert -- . --.

Column 5, line 7, change "to sea the" to

--to seal the--.

Column 5, line 12, after "above", insert -- , --.

Signed and Sealed this

Thirteenth Day of October, 1992

*Attest:*

DOUGLAS B. COMER

*Attesting Officer*         Acting Commissioner of Patents and Trademarks